US005480437A

United States Patent [19]
Draenert

[11] Patent Number: 5,480,437
[45] Date of Patent: Jan. 2, 1996

[54] PRESTRESSED SURGICAL NETWORK

[76] Inventor: Klaus Draenert, Gabriel-Max-Str., 8000 Munich 90, Germany

[21] Appl. No.: 928,158

[22] Filed: Aug. 10, 1992

Related U.S. Application Data

[63] Continuation of Ser. No. 534,330, Jun. 5, 1990, which is a continuation of Ser. No. 348,579, Apr. 27, 1989, abandoned.

[51] Int. Cl.$^6$ ........................................................ A61F 2/28
[52] U.S. Cl. .............................................. 623/16; 623/23
[58] Field of Search .................................. 623/11, 12, 1, 623/16, 18, 20, 22, 23, 66; 606/65, 73

[56] References Cited

U.S. PATENT DOCUMENTS

| | | | |
|---|---|---|---|
| 4,437,191 | 3/1984 | van der Zel et al. | 623/16 |
| 4,605,414 | 8/1986 | Gzajka | 623/16 |
| 4,668,233 | 5/1987 | Seedhom et al. | 623/16 |
| 4,735,625 | 4/1988 | Davidson | 623/16 |

FOREIGN PATENT DOCUMENTS

| | | | |
|---|---|---|---|
| 0016480 | 10/1980 | European Pat. Off. | 623/22 |
| 0077868 | 5/1983 | European Pat. Off. | 623/22 |
| 2842847 | 4/1980 | Germany | 623/72 |
| 3125658 | 1/1983 | Germany | 623/22 |
| 3445738 | 6/1986 | Germany. | |
| 3445731 | 6/1986 | Germany | 623/16 |

OTHER PUBLICATIONS

Histo–Morphologie des Bewegungsapparates 3, Art and Science, Munich, 1987.
Subjective Standpoints in Architecture and Science; Institute for Lightweight Structure, (IL) University of Stuttgart, Director Frei Otto.
Manual der Osteosynthese, Springer Verlog, Heidelberg, Berlin, New York 1969 Muller, Allgower and Willenegger.
K. Draenert: Some New Observations to Improve the Bone–To–Cement Contract, Nicholas Andry Award Paper, presented at the 38th Annual Meeting of the Association of Bone and Joint Surgeons held in Vancouver, May 27–31, 1986.

Primary Examiner—David Isabella
Attorney, Agent, or Firm—Kinney & Lange

[57] ABSTRACT

The invention relates to a surgical support or network for anchoring endoprostheses and/or reinforcing the bone cement used for anchoring endoprostheses. The support or network is designed as a prestressable prosthesis quiver (1) made of one or more layers of threads so that when prestressed, for example by means of a bone dowel (2) and a titanium cap (6), it can be anchored in the bony bed.

13 Claims, 2 Drawing Sheets

PRESTRESSED SURGICAL NETWORK

This is a continuation of application Ser. No. 07/534,330 filed on Jun. 5, 1990, abandoned as of the date of this application, which is a continuation of application Ser. No. 07/348,579, filed on Apr. 27, 1989, abandoned as of Jun. 5, 1990.

BACKGROUND OF THE INVENTION

1. Field of the Invention.

The invention relates to a surgical support or network for suspending or anchoring an implant in the bone or for reinforcing the bone cement used to anchor the components of prostheses.

2. DESCRIPTION OF THE PRIOR ART.

Usually, the components of joint replacements are anchored in the bone by means of a cold-polymerising polymethyl methacrylate (PMMA) or by locking them directly into the bone without bone cement. Recently, one has tried to anchor implant components more physiologically by means of pretensioned constructions (A. H. Huggler: Die Druckscheibenprothese im siebten Jahr ihrer klinischen Anwendung, in K. Draenert and A. Rütt (publishers); Histo-Morphologie des Bewegungsapparates 3, Art and Science, Munich, 1987).

The attempts to anchor the components of artificial joint replacements often fail because the forces cannot be transferred to the bone evenly. The result is that in cement-free components with a high modulus of elasticity, the presence of stress concentration (tension peak) in those areas which carry the main load leads to the consolidation of the bone, whereas the remaining bone segments atrophy as they are no longer made use of. In the case of cemented components, the bone cement fails to bear the very heavy loads permanently and therefore ruptures with the ultimate result that the components of the joint replacement become loose. of all the occurring forces, it is the shearing forces which have the most detrimental effect on the differentiation and development of the pluripotent mesenchyme, i.e. the mesenchyme tissue which ultimately produces the bone-forming cells known as osteoblasts.

There are constructions known from the field of architecture and statics with which one has attempted to use prestress in order to overcome these detrimental shearing forces, i.e. by reinforcing the concrete constructions with prestressed metal networks which take up the tensile strength (prestressed concrete). It is also possible to use free, pretensioned supports, such as light plane load-bearing structures, to convert tensile forces into pressure forces or compressive forces (Frei-Otto: Natürlichea Konstruktionen, Freie Verlagsanstalt, Stuttgrat, 1982). In the surgical locomotor system, too, several attempts have been made to adopt these principles, but they have been restricted to osteosynthesis, i.e. the use of screws in fracture treatment (Müller, Allgöwer and Willenegger, Manual der Osteosynthese, Springer Verlag, Heidelberg, Berlin, New York, 1969).

Constructions made of metal or carbon which reinforce the bone cement have already been used in the field of prosthetics, for example networks around the shafts of prostheses as described in U.S. Pat. No. 4 064 567. These networks do not form a close stocking and are not flexible. Due to their construction, they cannot not contact the bony bed of the prosthesis and thus their overall construction constitutes a prosthesis component in itself.

U.S. Pat. No. 4,457,028 describes multilayer, stocking-like reinforcements in the form of surgical networks which are partially absorbable and have a predetermined mesh size and filament thickness. These networks are excellent for reinforcing the cement stocking of a prosthesis, but are almost incapable of taking up the unfavourable shearing forces which occur in the interface between the prosthesis components and the bone. Furthermore, on account of the low affinity of the pure wire reinforcements described in DE-A-2 917 446 to the PMMA of the bone cement, they cannot achieve ideal contact with the cement matrix and can lead to filling effects which, in turn, represent predetermined breaking points. Hence when under heavy strain, the reinforcement can begin to wander and destroy the matrix. The absorbable materials according to U.S. Pat. No. 4,365,357 keep the bone in place; however, they may not be in a position to enable long-term load transmission from the prosthesis component to the bone.

Also, long-term studies have shown that conventional bone cement can excellently stand up to pressure in the body, and that for over 20 years, but it is not sufficiently resistant to tensile stress and bending stress and can collapse under the strain within a short period of time.

SUMMARY OF THE INVENTION

The object underlying the invention is thus to provide means for anchoring endoprostheses and/or for reinforcing the bone cement used to anchor the endoprostheses, with which means the tensile and bending stress acting on the bony bed and the bone cement can be converted into compressive forces.

This object is achieved with the present invention. According to the invention, the bone cement is reinforced or the implant suspended in the bony bed in such a way that only compressive forces occur. The implantation of the surgical support or network of the invention eliminates the damaging shearing forces, thus considerably prolonging implantation life.

Hence the subject matter of the invention is a surgical support or network which can be tensioned or braced in the bone in such a manner that the forces which act on the prosthesis components can be evenly transferred to the bony bed.

The support or network of the invention is designed as a stocking and consists of at least one thread which is knitted into this network. The thread itself is preferably flexible; but in any case, the stocking-shaped network made of the thread should be flexible in the longitudinal direction, so that when under tension in the bone, it can be elongated by preferably at least 5%, more preferably 10 to 20%, of its total length when not under strain. The stocking of the support or network can be open or closed at its lower end.

The stocking-shaped network can comprise a single layer. The multilayered embodiment, however, which is obtainable for instance by folding back the stocking arranged on a cylinder once or more often as is described in U.S. Pat. No. 4,365,357, exhibits greater stability and strength. Specifically, the embodiment of the network can be adapted to the biomechanical demands. The following description is mainly based on the example of a hip joint prosthesis, but the support or network of the invention can be used for all joint replacement components, for example in the knee, ankle or elbow joint.

The support or network of the invention is designed such that it can be prestressed with the result that when suspended in the bony bed or when the bone cement is applied to the bony bed, it is elongated and remains in this elongated position.

Various means can be provided for inducing prestress. As an example, one end of the stocking can be locked, for instance, into the medullary cavity of the proximal femur with a self-blocking plastic material, and the other end can be drawn across the metaphysis either manually or by means of a tensioning apparatus where it is then fastened under tension or stress with screws, pins, dowels or special bone dowels which are described, for instance, in U.S. Pat. No. 5,084,050.

In a further embodiment, the thread from which the network is made can exhibit the form of a bead chain, i.e. the thread can, for example, exhibit several successive bead-shaped thickenings or enlargements, which can be formed during extrusion of the thread, or the beads can be pressed onto the thread, for example by means of the HIP method (High Isostatic Pressure method). These beads preferably have a diameter of about 0.5 to 3 mm preferably 1 to 2 mm, and are spaced at a distance of preferably about 0.5 to 2 cm. Beads of this diameter can also be used as positioners for the corresponding thickness of the cement layer. With the network being constructed of bead chains of this diameter, a high resistance builds up at the beads when the bone cement is applied. This resistance leads to an extension (elongation) of the stocking-shaped network and thus to its being prestressed. Depending on the viscosity of the cement, one can optionally use beads of a smaller diameter, too, but the beads should always be greater than 200 µm in diameter. If the diameter of the beads is smaller, the network will not be prestressed to sufficient a degree.

It is also possible to provide parts of the stocking-shaped network with lateral extensions, and to pull out the lateral extensions or projections of the network through diagonal bores positioned at various levels of the prosthesis shaft, and optionally also below its tip, and then prestress them there three-dimensionally, for example by means of screws or seams.

Prestress can also be achieved by exerting pressure onto the network or support from the interior of the stocking, and thus elongating it. This can be carried out for example by means of a suitably shaped, inflatable balloon inserted into the stocking.

The above described prestressing of the network enables very uniform load transmission to the bone.

It is particularly advantageous to use "isogenic" materials for the network used to reinforce the bone cement, preferably, materials of the same chemical origin as the bone cement or exhibiting chemical affinity to the bone cement and/or being in a position to enter into a chemical reaction with the liquid bone cement. As all the bone cements presently in use in the surgery of the locomotor system are cold-polymerising polymethyl methacrylates, "isogenic" materials are mainly acrylate filaments or acrylate-coated metal threads and wires. The threads of the network according to the invention are thus preferably made of acrylate, methacrylate, PMMA and/or the copolymers or derivatives thereof and/or a plastic material affinitive to the acrylates.

Depending on the strain put on the construction as a whole, it may be especially advantageous to use reinforced acrylate threads, for example metal threads coated with acrylate. The metal threads can be either monofilic or, when under particularly heavy strain, polyfilic. Titanium or surgical steel wire of a certain elasticity are especially suitable metals, e.g. the sterile metal wire EH7602 produced by Ethicon. When the secondarily polymerising matrix of the bone cement enters into a chemical reaction with such a network, it enables much higher and more reliable load transmission from the prosthesis component to the cement and from the cement to the bone, but also from the reinforcement directly to the bone. In the latter case, it is of particular advantage if the coating of the metal, in turn, provides for an attenuation of the direct introduction of forces into the bone. However, within the scope of this invention it is also possible to use metal threads, such as titanium or surgical steel wire, as the material for the network.

The network material is preferably "isoelastic", i.e. it has approximately the same elastic constants as the bone cement, thus enabling particularly good load transmission.

The thickness of the thread depends on the material used and is preferably about 100 to 700 µm. When using acrylate, the thread thickness is preferably about 100 to 300 µm, most preferably about 200 µm, when using titanium preferably about 200 to 500 µm, most preferably about 400 µm, when using surgical steel more than 50 µm, preferably about 100 to 300 µm, most preferably about 200 µm. The mesh width or thickness is about 0.5 to 10 mm, preferably about 1 to 4 mm, most preferably about 1.5 mm.

Due to the partial installation of absorbable networks, the absorption of these structures and the bone growth that follows render it possible to enlarge the surface of the bone that takes up the forces. Particularly suitable examples of absorbable materials are organic polymers, such as catgut or another collagen, a synthetic polylactide, polyglycolide or another polyamino acid derivative or related polymer and/or a mixture of various organic polymers. The absorbable materials are preferably applied in the proximal portion and/or in the outermost layer of the network. If the threads carry beads or are designed as bead chains, it is especially advantageous to use sintered apatite beads or beads made of a composite containing tricalcium phosphate. This has the advantage that the beads act as modelling elements for the formation of physiological bone honeycomb, and that apatite's high affinity to the bone cell provides particularly favourable material properties (see K. Draenert: Some New Observations to Improve the Bone-to-Cement Contact, Nicholas Andry Award Paper, presented at the 38th Annual Meeting of the Association of Bone and Joint Surgeons held in Vancouver, May 27 to 31, 1986). A further advantage is that sintered, hard fillers also initiate the positive, biomechanical induction of bone growth as has been shown in animal experiments.

It is of advantage to space the individual layers of the network in the radial direction of the stocking by means of at least one spacer, for example a tension ring, at a predetermined distance. The distance is about 0.5 to 5 mm, preferably about 1 mm.

With the support or network of the invention, orthopaedists and surgeons have a material which advantageously solves the problems caused by imparting strain onto the cement and, in the case of cement-free implants, those caused by the occurrance of tension peaks (stress concentration).

The following is a more detailed description of the invention with reference to examples and the accompanying drawings in which

EXAMPLE 1

In order to prepare a support or network for receiving a femoral joint replacement component for the hip joint, 100 m of surgical titanium wire having a thread thickness of 400 μm is placed in a commercial circular knitting machine and knitted into an endless stocking. The mesh width is adjusted to about 1 to 2 mm, the stocking comprising 14 meshes along its circumference. By pulling the stocking over a tension ring, one obtains a two-layer stocking which exhibits constant layer distances at the proximal end by means of a second tension ring. The stocking is anchored in the bony bed with an adjustable prestress by screwing the proximal ring into position via screw holes in the bone provided for this purpose and by tensioning the distal ring by locking it in the medullary cavity.

EXAMPLE 2

100 m of a 400 μm thick titanium wire is coated with acrylate in a dipping process and then dried. It is then rolled up and prepared for further processing in a circular knitting machine. 50 of the thus coated wire is rolled up onto the spools of the circular knitting machine and knitted into a network. The network has a mesh width of about 1 mm, and the stocking-shape network comprises 40 meshes along its circumference. The network is rolled over a tension ring and the free end of the circular knitted network is fastened by means of a tensionable ring or a bone dowel. The ring is provided with screw holes to receive bone screws.

EXAMPLE 3

Beads made of tricalcium phosphate and 1 mm in diameter are pressed at spaces of 2 cm onto a 400 μm thick titanium wire using the HIP method. The thus obtained bead chain is rolled onto the spools of a circular knitting machine in the above described manner, with the exception that in this case the needles of the machine are not adjusted to the thread thickness, but to the beads. Further processing is as described above.

Working Example 1

Figure 1:
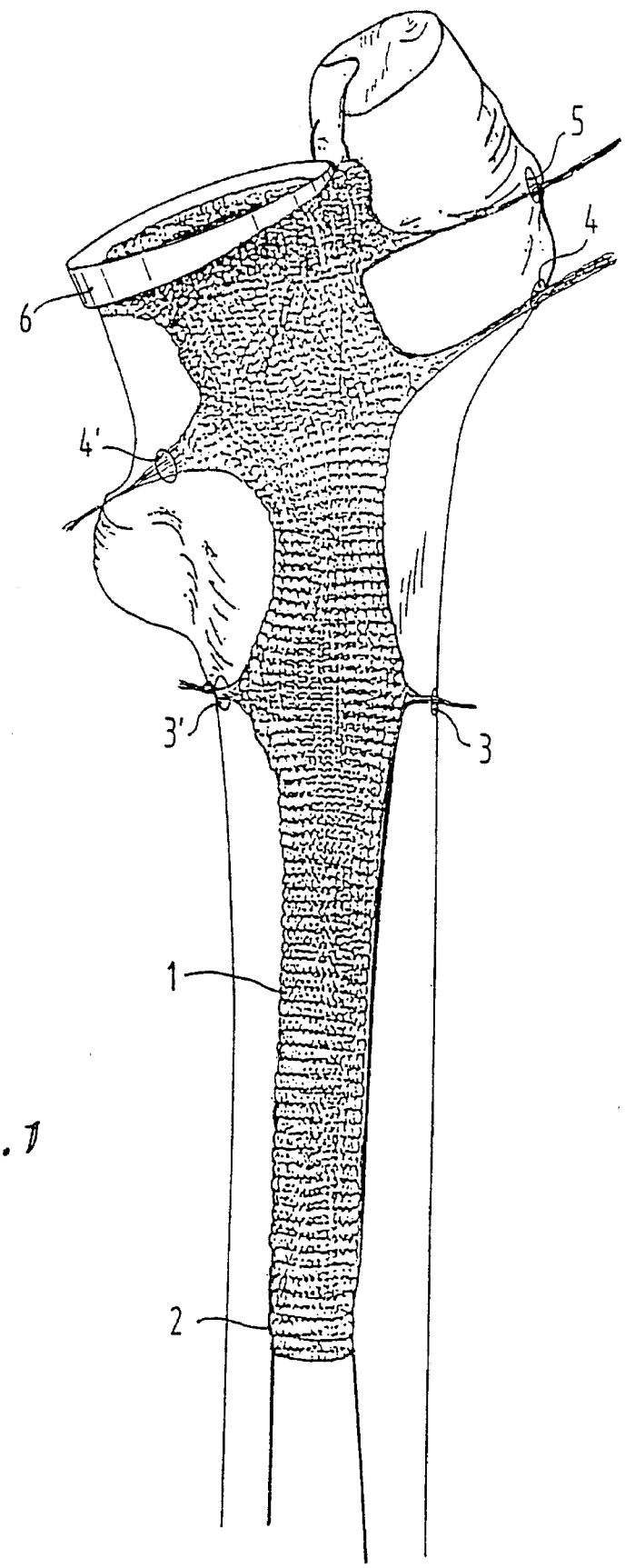
FIG. 1 shows the network of the invention in the form of a two-layer stocking and FIG. 2 shows a mesh-shape reinforcement for the acetabulum, according to the invention.

FIG. 1 shows a two-layer stocking 1 whose tip is fastened in the medullary cavity by means of an interlocking bone dowel 2. The stocking is pulled in an outward direction through drill holes 3, 3', 4, 4', 5 arranged in three tiers on top of one another, is then fastened and prestressed. After having been prestressed with a tensioning instrument, the proximal end is fastened above the neck of the femur with a titanium cap 6. The cap can also be used as a spacer between the layers of the network.

Working Example 2

A pathological hip joint is treated to receive a joint replacement. According to the preoperative plan, the head of the hip bone is resected at the appropriate height, and the medullary cavity of the femur is laterally opened with a diamond concave cutter. It is advantageous to open the medullary cavity before resecting the head and neck of the femur. When preparing the bony bed, it is also necessary to carefully flush out the medullary cavity under pressure. This is followed by making a drainage issue at the anterolateral circumference of the femur using a trokar positioned distal to the tip of the prosthesis together with a 4.5 mm thick drill, a drill guide and a pneumatic drill. A self-tapping cannula is inserted through the drill guide and into the drill hole. The surgical network prepared according to Example 1 is then inserted into the medullary cavity of the femur using a washed spongiosa cylinder and is distally locked in the medullary cavity using a pestle. By means of a tensioning apparatus, the network is subjected to prestress (elongation) by mounting the proximal ring onto the proximal opening of the femur and screwing it into position. This is followed by hermetically sealing the medullary cavity with a rubber gasket by applying a cement syringe, as described, for instance, in U.S. Pat. No 4,671,263. By applying vacuum to the distal drainage issue and simultaneously emptying the cement syringe, bone cement is forced through the network into the bone. This is then followed by introducing the prosthesis component which is not touched any more until the bone cement has completely hardened.

Working Example 3

A simple and effective network for reinforcing the bone cement is prepared in such a manner that 100 m of a 200 mm thick acrylate fibre, for example a commercial optical fibre, is knitted into a circular knitted fabric by means of a circular knitting machine. The circular fabric exhibits a mesh width of about 1.5 mm and has 50 meshes along its circumference. This acrylate fibre net is pulled over a tension ring of a diameter of 44 mm, and the free end of the net is doubled over a ring 16 mm in diameter after four layers. This network can be used for cases of severe arthrosis as described in working example 2. In such cases the acetabulum of the affected hip joint is freed of any residual cartilage and using a hollow diamond grinder having a diameter of 16 mm, as described for instance in U.S. Pat. No. 4,895,146, an anchoring hole is made in the supporting roof of the acetabulum. The stocking of the support or network is then fastened in the pelvis by means of a screwable dowel in the direction toward the sacro-iliac joint, i.e. the joint via which the load is transmitted to the spine. The network is then prestressed by means of a tensioning apparatus and is screwed into position by means of the tension ring at the edge of the acetabulum. Once the bony bed has been carefully flushed out, a drainage screw is inserted starting at the lateral edge of the acetabulum, and bone cement is applied under the suction of the vacuum applied via the drainage screw. The prosthesis is carefully implanted into the thus prepared and applied bone cement.

Figure 2:
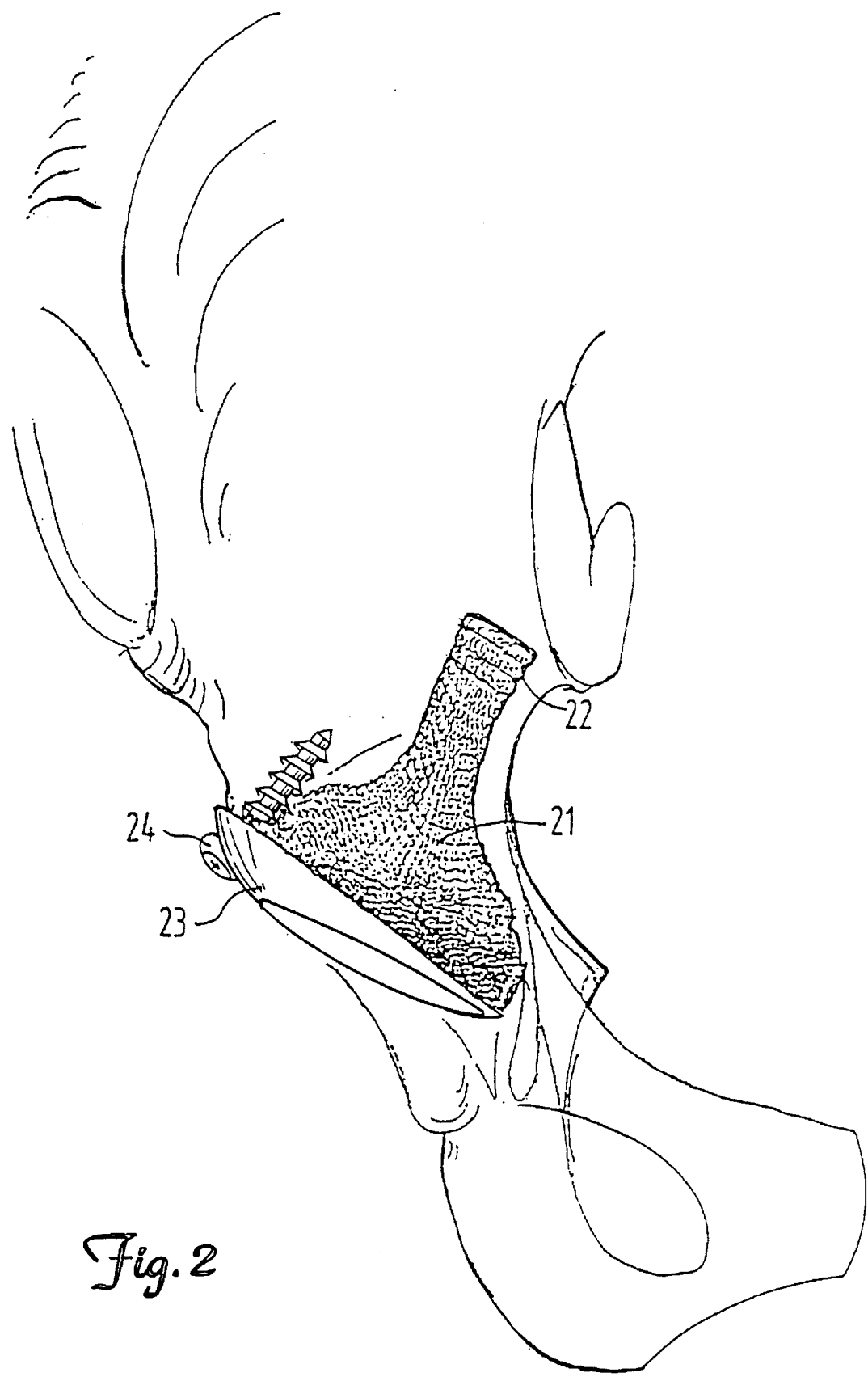

FIG. 2 shows such an acetabular mesh reinforcement 21. The end of the stocking is threaded through a grinding hole which is 16 mm in diameter and is fastened in the pelvis by means of a bone dowel 22. This is followed by prestressing the network using a tensioning apparatus and fastening it at the edge of the pelvis with a titanium ring 23 by means of a bone screw 24. The bed is now ready to receive the bone cement and the prosthesis.

I claim:

1. A surgical network for anchoring an endoprosthesis and reinforcing bone cement used for anchoring the endoprosthesis in a bony bed wherein the network comprises a continuous prestressable prosthesis stocking made of at least one layer of threads and means for prestressing and anchoring the network in the bony bed under prestress, wherein the stocking is elongate and has two ends, wherein the stocking is open at least one end thereof such that the stocking is adapted to receive the endoprosthesis through the open end thereof while the network is anchored under prestress in the bony bed. This is a continuation of application Ser. No. 07/534,330 Filed on Jun. 5, 1990, abandoned as of the date of this application, which is a continuation of application Ser. No. 07/348,579, filed on Apr. 27, 2989, abandoned as of Jun. 5, 1990.

2. The network according to claim 1, wherein the threads are made of a material selected from the group consisting of metal, polymers and polymer-coated threads.

3. The network according to claim 1, wherein the threads are made of a material selected from the group consisting of a monofilic and a polyfilic wire, the threads being made of titanium and being coated with a coating selected from the group consisting of acrylate, methacrylate, polymethacrylate and a related derivative of acrylates.

4. The network according to claim 1, wherein the threads are a material selected from the group consisting of acrylate, methacrylate, polymethyl methacrylate, copolymers, copolymer derivatives, and a synthetic material which is chemically affined to the acrylates.

5. The network according to claim 1, wherein the support is at least partially absorbable, the absorbable material being an organic polymer selected from the group consisting of catgut, a collagen, synthetic polylactide, polyglycolide and mixtures thereof.

6. The network according to claim 1, wherein the threads consist of bead chains whose beads have a diameter of about 500 to 3000 μ.

7. The network according to claim 6, wherein the bead chains are made of a material selected from the group consisting of ceramics, apatite, tricalcium phosphate derivatives, sintered calcium phosphate, non-sintered calcium phosphate, a biocompatible metal and a coated metal.

8. The network according to claim 1, wherein the prestressable stocking is prestressable in tiers and the means for prestressing and anchoring the network are selected from the group consisting of screws, clamps, bone dowels, pins and seams.

9. The network according to claim 8, wherein at least one of the bone dowels is a self-locking dowel and is made of a material selected from the group consisting of a biocompatible plastic material, metal and a bone transplant.

10. The network according to claim 1 wherein the stocking is made of more than one layer of threads, the network comprising spacers which separate the individual layers at a predetermined distance of 0.5 to 5 mm.

11. The network according to claim 1 wherein the means for prestressing and anchoring the network comprise means for exerting pressure on an interior of the stocking thereby prestressing the stocking.

12. The network according to claim 1, wherein the means for prestressing and anchoring the network include means for prestressing the stocking at one of the stocking's two ends, the means being selected from the group consisting of screws, clamps, bone dowels, pins and seams.

13. A surgical network for anchoring an endoprosthesis and reinforcing bone cement used for anchoring the endoprosthesis, wherein the network comprises a continuous prestressable stocking having two ends and being open at least one of the ends, the stocking having at least one layer of threads, the network further comprising means for prestressing the stocking to an elongated prestressed position in a bony bed such that tensile and bending stresses acting on the bony bed and bone cement are converted into compressive forces which the endoprosthesis is to be anchored.

* * * * *

UNITED STATES PATENT AND TRADEMARK OFFICE
CERTIFICATE OF CORRECTION

PATENT NO. : 5,480,437
DATED : January 2, 1996
INVENTOR(S) : KLAUS DRAENERT

It is certified that error appears in the above-indentified patent and that said Letters Patent is hereby corrected as shown below:

On title page,
at [63] under "Related U.S. Application Data" after "Ser. No. 348,579, Apr. 27, 1989, abandoned", insert --,based on PCT EP88/00761 filed Aug. 25, 1988.-- at [30] insert --Foreign Application Priority Data Aug. 27, 1987 [DE] Fed. Rep. of Germany P3728686.2--

Signed and Sealed this

Thirteenth Day of August, 1996

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,480,437
DATED : January 2, 1996
INVENTOR(S) : KLAUSE DRAENERT

It is certified that error appears in the above-indentified patent and that said Letters Patent is hereby corrected as shown below:

Col. 1, line 52, delete "Natürlichea", insert --Natürliche--

Col. 6, line 65, after "bed", delete "This is a continuation of application Ser. No. 07/534,330 Filed on Jun. 5, 1990 abandoned as of the date of this application, which is a continuation of application Ser. No. 07/348,579, filed on Apr. 27, 2989, abandoned as of Jun. 5, 1990.", insert after "bed" --such that tensile and bending stresses acting on the bony bed and bone cement are converted into compressive forces.--

Col. 7, line 24, after "µ", insert --m--

Signed and Sealed this

Twenty-fourth Day of September, 1996

Attest:

BRUCE LEHMAN

Attesting Officer  Commissioner of Patents and Trademarks